United States Patent [19]
Fagerström et al.

[11] Patent Number: 5,922,579
[45] Date of Patent: *Jul. 13, 1999

[54] XYLANASES AND USES THEREOF

[75] Inventors: Richard B. Fagerström, Espoo; Marja Paloheimo, Vantaa; Raija Lantto, Klaukkala; Tarja Lahtinen, Vantaa; Pirkko Suominen, Helsinki, all of Finland

[73] Assignee: Röhm Enzyme Finland OY, Rajamäki, Finland

[21] Appl. No.: 08/768,374

[22] Filed: Dec. 17, 1996

Related U.S. Application Data

[60] Provisional application No. 60/008,746, Dec. 18, 1995.

[51] Int. Cl.$^6$ .............................. C12P 19/14; C12S 3/08; D21C 3/00
[52] U.S. Cl. ........................... 435/99; 435/274; 435/277; 435/278; 162/70; 162/71; 162/72
[58] Field of Search ............................. 435/99, 278, 277, 435/274; 162/70, 71, 72

[56] References Cited

U.S. PATENT DOCUMENTS 5,298,405  3/1994  Nevalainen et al. ..................... 435/209

FOREIGN PATENT DOCUMENTS

| 2154945 | 1/1996 | Canada . |
| 0 406 617 | 1/1991 | European Pat. Off. . |
| 2-119790 | 5/1990 | Japan . |
| WO 91/05908 | 5/1991 | WIPO . |
| WO 93/19171 | 9/1993 | WIPO . |
| WO 93/24621 | 12/1993 | WIPO . |
| WO 95/12668 | 5/1995 | WIPO . |
| WO 96/23062 | 8/1996 | WIPO . |

OTHER PUBLICATIONS

ATCC Catalogue of Fungi/Yeasts, 17th Edition, p. 96, 1987.
Alconada, T.M. and M.J. Martínez, "Purification and characterization of an extracellular endo–1,4–β–xylanase from *Fusarium oxysporum* f. sp. melonis," *FEMS Microbiol. Lett.* 118(3):305–310 (May 1994).
Aono, R., "Thermostable Alkaline Xylanases Produced by Alkaliphilic Strains of Bacillus spp.," *Kami Pa Gikyoshi* 48(9):1148–1166 (1994).
Bailey, M.J. et al., "Interlaboratory testing of methods for assay of xylanase activity," *J. Biotechnol.* 23(3):257–270 (1992).
Bajpai, P. and P.K. Bajpai, "Biobleaching of Kraft Pulp," *Process Biochem.* 27(6):319–325 (1992).
Christakopoulos, P. et al., "Purification and characterization of two low molecular mass alkaline xylanases from *Fusarium oxysporum* F3," *J. Biotechnol.* 51(2):181–189 (Nov. 1996).

Dubeau, H. et al., "Xylanase of *Chaetomium cellulolyticum*: Its Nature of Production and Hydrolytic Potential," *Biotechnol. Lett.* 9(4):275–280 (1987).
Farrell, R.L., et al., "New bleach sequences of kraft pulp using white white–rot fungi," in *Ligno–cellulosics: Science, Technology, Development and Use*, Kennedy, J.F. et al., Eds, E. Horwood; New York, pp. 305–315 (1992).
Gandhi, J.P., et al., "Characterization of Extracellular Thermostable Xylanase From *Chaetomium globosom*," *J. Chem. Tech. Biotechnol.* 60(1):55–60 (May 1994).
Ganju, R.K. et al., "Purification and characterization of two xylanases from *Chaetomium thermophile* var. *coprophile*," *Can. J. Microbiol.* 35:836–842 (1989).
Gilkes, N.R. et al., "Domains in Microbial β–1,4–Glycanases: Sequence Conservation, Function, and Enzyme Families," *Microbiological Rev.* 55(2):303–315 (1991).
Irie, T. et al., "Purification of xylanase from *Chaetomium gracile* Mutant 1161 and its xylobiose–forming properties," *Hakkokogaku* 70(2):109–114 (1992).
Jurasek, L., "Direct biological bleaching of pulps," in *Ligno–cellulosics: Science, Technology, Development and Use*, Kennedy, J.F. et al., Eds, E. Horwood; New York, pp. 317–325 (1992).
Kantelinen, A. et al., "Hemicellulases and Their Potential Role in Bleaching," in *Tappi Proceedings: 1988 Intl. Pulp Bleaching Conf.*, Jun. 5–9, Orlando, pp. 1–9 (1988).
Karhunen, T. et al., "High frequency one–step gene replacement in *Trichoderma reesei*. I. Endoglucanase I overproduction," *Mol. Gen. Genet.* 241(5–6):515–522 (1993).
Kawaminami, T. and H. Iizuka, "Studies on Xylanase from Microorganisms. (IV) Action of Xylanase of *Chaetomium trilaterale* Strain No. 2264 upon Xylan," *J. Ferment. Technol.* 48(3):161–168 (1970).
Onysko, K.A., "Biological Bleaching of Chemical Pulps: A Review," *Biotech. Adv.* 11:179–198 (1993).
Rajarm, S. and A. Varma, "Production and characterization of xylanase from *Bacillus thermoalkalophilus* grown on agricultural wastes," *Appl. Microbiol. Biotechnol.* 34:141–144 (1990).
Senior, D.J. and J. Hamilton, "Use of Xylanases to Decrease the Formation of AOX in Kraft Pulp Bleaching," *J. Pulp Paper Sci.* 18(5):J165–J169 (1992).

(List continued on next page.)

*Primary Examiner*—Francisco Prats
*Attorney, Agent, or Firm*—Sterne, Kessler, Goldstein & Fox P.L.L.C.

[57] ABSTRACT

Enzyme compositions containing thermostabile xylanases of *Chaetomium thermophilum*, purified enzyme preparations of such xylanases, and the use of such compositions and preparations in the bleaching of plant pulp and in feed and baking applications are described.

30 Claims, 6 Drawing Sheets

OTHER PUBLICATIONS

Viikari, L. et al., "Bleaching With Enzymes," in *Proceedings of 3rd Intl. Conf. on Biotech. in the Pulp and Paper Indust.*, Stockholm, pp. 67–69 (1986).

Viikari, L. et al., "Application of Enzymes in Bleaching," in *Proceedings of 4th Intl. Symp. on Wood and Pulping Chem.*, Paris, pp. 151–154 (1987).

Viikari, L. et al., "Xylanase," *Paper and Timber* 73(5):384–389 (1991).

Viikari, L. et al., "Hemicellulases for Industrial Applications," in *Bioconversion of Forest and Agricultural Plant Residues*, Saddler, J.N., Ed; CAB International, Wallingford, pp. 131–182 (1993).

Viikari, L. et al., "Xylanases in bleaching: From an idea to the industry," *FEMS Microbiol. Rev.* 13(1):335–350 (Jan. 1994).

Wong, K.K.Y. et al., "Multiplicity of β–1,4–Xylanase in Microorganisms: Functions and Applications," *Microbiological Rev.* 52(3):305–317 (1988).

Yoshino, S. et al., "Two family G xylanase genes from *Chaetomium gracile* and their expression in *Aspergillus nidulans*," *Curr. Genet.* 29(1):73–80 (Dec. 1995).

GenBank report for EMBL search, Accession No. Z49892, from Perez–Gonzalez J.A. et al., "*A. nidulans* gene for xylanase," submitted Jun. 1995.

GenBank report for NCBI Entrez search, Accession No. D49850, from Tsukagoshi, N., "*Chaetomium gracile* endo–beta1, 4–xylanase A (cgxA) gene, complete cds," submitted Mar. 1995.

GenBank report for NCBI Entrez search, Accession No. D49851, from Tsukagoshi, N., "*Chaetomium gracile* endo–eta1, 4–xylanase B (cgxB) gene, complete cds," submitted Mar. 1995.

GenBank report for NCBI Entrez search, Accession No. L25310, from Stalbrand H. et al., "*Trichoderma reesei* beta–mannanase mRNA, complete cds," submitted 1993.

GenPept report for NCBI Entrez search, Accession No. A44595, from Yaguchi, M., "endo–1, 4–beta–xylanase (EC 3.2.1.8) IIB (proteinase–sensitive)—fungus (*Trichoderma viride*)," submitted Mar. 1994.

English language abstract of Japanese Patent No. 2–119790, DIALOG WPI Acc. No. 90–182390/199024 (1990).

Grant, R., "R&D optimizes enzyme applications," *Pulp and Paper Intl.*, pp. 56–57, Sep. 1993.

Pérez–González, J. A. et al., "Molecular Cloning and Expression in *Saccharomyces cerevisiae* of Two *Aspergillus nidulans* Xylanase Genes," *Appl. Environ. Microbiol.* 62(6):2179–2182 (Jun. 1996).

XYLANASES AND USES THEREOF

CROSS-REFERENCE TO RELATED APPLICATION

The present application claims priority to prior U.S. provisional application No. 60/008,746, filed Dec. 18, 1995.

BACKGROUND OF THE INVENTION

1. Field of the Invention

The present invention is in the area of thermostable enzymes, and the use of same. Especially, the invention is in the area of Chaetomium xylanases that are active at a high temperature. The compositions of the invention are useful to modify plant biomass properties. The invention is also directed to a method for enzyme-aided bleaching using the enzyme compositions of the invention. Furthermore, the invention concerns the use of the novel enzyme compositions in feedstuffs and flour compositions.

2. Description of Related art

Plant biomass is a composite material consisting primarily of a matrix of cellulose, hemicellulose, and lignin. Enzymes degrading e.g. the hemicellulose xylan, xylanases, can be used in animal feed compositions which are rich in arabinoxylans and glucoxylans, in baking, and for bleaching of cellulosic pulps.

Thus, when added to feeds for monogastric animals (e.g. poultry or swine) which contain cereals (e.g. barley, wheat, maize, rye or oats) or cereal by-products, a hemicellulolytic enzyme improves the break-down of plant cell walls which leads to better utilization of the plant nutrients by animal. This leads to improved growth rate and feed conversion. Also, the viscosity of the feeds containing xylan can be reduced.

In baking applications small amounts of xylanases added to the flour impart favorable characteristics to the dough and to the bread itself. Such characteristics include e.g. increased loaf volume and better textural characteristics (break and shred quality and crumb quality).

In the pulp and paper industry xylanases and other hemicellulases are used, e.g., to improve the bleachability of the pulp.

The aim of kraft pulp bleaching is to remove the residual lignin that is left in pulp after kraft cooking. Traditionally, this has been done using chlorine-containing chemicals. Because of environmental concerns and consumer demands, alternative bleaching technologies have been desired.

The first biotechnical approach to this problem was to attack the lignin directly with lignin degrading enzymes. However, the chemistry of enzymatic lignin degradation seems to be very complicated and difficult to control.

Lignin can be degraded, if the whole microorganism that produces ligninases is used. However, treatment times are relatively long. For example, treatment times may take days, and the microorganisms need supplemental nutrients to work. It can also be difficult to control the growth of other, undesired, microbes. Lignin degradation by using ligninases or by microorganisms is the subject of much research. (see, for example, Farrell, R. L. et al., *Lignocellulosics* 305–315 (1992); Jurasek, L., *Lignocellulosics* 317–325 (1992)).

In addition to cellulose and lignin, wood pulp contains hemicellulose. Another approach to lignin removal is to attack hemicellulose—the third main component of wood. The hemicellulose in native hardwood is mainly xylan, while in softwood the hemicellulose is mainly glucomannans and some xylan. During kraft cooking, part of the xylan is dissolved into the cooking liquor. Towards the end of the cooking period when the alkali concentration decreases, part of the dissolved and modified xylan reprecipitates back onto the cellulose fiber.

In 1986, it was noticed that xylanase pretreatment of unbleached kraft pulp results in a lessened need for chemicals in the bleaching process (Viikari, L. et al., Proceedings of the 3rd Int. Conf. on Biotechnology in the Pulp Paper Ind., Stockholm (1986), pp. 67–69). Xylanase pretreatment of kraft pulp partially hydrolyses the xylan in kraft pulp. This makes the pulp structure more porous and enables more efficient removal of lignin fragments in the subsequent bleaching and extraction stages. Later, in several laboratories, the xylanase pretreatment was reported to be useful in conjunction with bleaching sequences consisting of $Cl_2$, $ClO_2$, $H_2O_2$, $O_2$ and $O_3$. See reviews in Viikari, L. et al., *FEMS Microbiol. Rev.* 13: 335–350 (1994); Viikari, L. et al., in: Saddler, J. N., ed., *Bioconversion of Forest and Agricultural Plant Residues*, C-A-B International (1993), pp. 131–182; Grant, R., Pulp and Paper Int. (September 1993), pp. 56–57; Senior & Hamilton, *J. Pulp & Paper:* 111–114 (September 1992); Bajpai & Bajpai, *Process Biochem.* 27:319–325 (1992); Onysko, A., *Biotech. Adv.* 11:179–198 (1993); and Viikari, L. et al., *J. Paper and Timber* 73:384–389 (1991).

As a direct result of the better bleachability of the pulp after such a xylanase treatment, there is a reduction of the subsequent consumption of bleaching chemicals, which when chloride containing chemicals are used, leads to a reduced formation of environmentally undesired organochlorine compounds. Also as a direct result of the better bleachability of pulp after a xylanase treatment, it is possible to produce a product with a high final brightness where such brightness would otherwise be hard to achieve (such as totally chlorine free (TCF) bleaching using peroxide). Because of the substrate specificity of the xylanase enzyme, cellulose fibers are not harmed and the strength properties of the product are well within acceptable limits.

However, in many of the practical applications, the use of xylanases is not straightforward; the xylanases must be active in the temperature and pH conditions of the process in which they are used. Formulation of commercial feed using pelleting, extrusion or expanding, often contains steps involving high temperatures (70–180° C.). Enzymes added to the formulation process should withstand these conditions. On the other hand, the corresponding temperature in the intestin of animals is about 40° C. Thus, ideal xylanases for feed compositions should withstand the above mentioned extream temperatures. In bleaching applications, xylanase application is not as simple as adding a xylanase treatment step. Because the bleaching process, and even the sequence of the steps used in the bleaching process varies in different pulp mills, there is thus a continous need to find new xylanases active in different temperature and pH conditions.

Most commercial xylanases designed for feed applications and pulp bleaching are not very thermo-tolerant, especially when neutral or alkaline pH conditions are used. In practice, xylanases are generally inefficient or inactive at temperatures higher than 60° C. and often these enzymes work under acidic conditions. Generally, there are differences in the physical characteristics of xylanases of fungi and bacteria (for review, see Wong et al., *Microbiol. Rev.* 52:305–317 (1988)). Typically, fungal xylanases have temperature optimum at about 50° C. and lower pH optimum than have those of bacterial origin. Xylanases of bacterial origin generally have a temperature optimum in the range of 50 to 70° C.

PCT/US90/05933 (WO 91/05908) proposes the use of xylanase in pulp bleaching together with chlorine or chlorine compounds. Chaetomium is proposed as a xylanase source. Screening for xylanase from Streptomyces and Chainia strains is described. Bleaching experiments were performed using xylanase preparations from Chainia sp. culture medium.

EP-A 0 406 617 proposes the use of xylanase in an enzymatic delignifying process of lignocellulosic material, especially after a ligninolytic enzyme. The xylanase may be derived form various sources, for example from Chaetomium. The use of xylanase from Chainia sp culture medium is exemplified.

Gandhi, J. P. et al., *J. Chem. Tech. Biotechnol.* 60:55–60 (1994) reported studies on thermostability and pH stability of crude xylanase preparations from *Chaetomium globosum*. The optimum temperature of the xylanase was found to be in the range of 50 to 60° C., while the optimum pH was found to be pH 5.0. The enzyme was reported not to lose any of the original activity between 40 to 60° C. for a period of 10 min and was reported to retain more than 70% of the original activity in the range of 70 to 100° C. for 10 min. The pH stability studies indicated that the enzyme retained all activity between pH 5 and 6 and more than 70% of the original activity over a wide range of alkaline pH values (7–10). It was suggested to use the culture filtrates for the treatment of cellulose pulps without further purification.

The xylanase of *Chaetomium cellulolyticum* and *Chaetomium trilaterale* have also been studied (Dubeau, H. et al., *Biotechnol. Lett.* 9:275–280 (1987) and Kawaminami, T. and Iitzuka, H. *J. Ferment. Technol.* 48:161–168 (1970), respectively). However, neither the thermostability nor the pH profile of the enzymes was reported. The xylanases were suggested to be of use in clarification of fruit juices. The use of these enzymes in pulp bleaching or as feed additive was not suggested.

Ganju, R. K. et al., *Can. J. Microbiol.* 35:836–842 (1989) reported the purification and characterization of two xylanases from *Chaetomium thermophile* var. *coprophile*. Two xylanases (I and II) out of several extracellular xylanases produced by *C. thermophile* var. *coprophile* were purified to homogeneity. These enzymes had molecular weights of 26,000 Daltons (xylanase I) and 7,000 Daltons (xylanase II). The temperature optima for xylanase I and II were 70 and 60° C., and they were optimally active at pH 4.8–6.4 and 5.4–6.9, respectively. The use of these xylanases in pulp bleaching or as feed additive was not suggested.

Irie et al., *Hakko Kogaku Kaishi* 70(2): 109–114 (1992) have reported the purification of a xylanase from a *Chaetomium gracile* mutant. The molecular weight was reported to be 19,000 daltons, and the xylanase contained two subunits: one having a molecular weight of 14,400 daltons and the other a molecular weight of 4,800 daltons. The pI was 8.35. The maximal xylobiose forming activity was found at pH 5.0 and 50° C. The pH range was reported to be pH 4.0–pH 7.0. Yoshino et al., *Curr. Genet.* 29:73–80 (1995) reported the isolation and sequencing of two xylanase genes from *Chaetomium gracile* wild and mutant strains and their expression in *Aspergillus nidulans*. The mature CgXA and CgXB xylanases contain 189 and 211 amino acids, respectively, and share 68.5% homology. The cgxA and cgxB genes were introduced into *Aspergillus nidulans* and reported to be expressed with their own promoters. The use of these *C. gracile* xylanases in pulp bleaching or as feed additive was not suggested.

SUMMARY OF THE INVENTION

Recognizing the importance of developing an environmentally safe and economical method of modifying plant biomass, the inventors have searched for new enzymes that would be useful in such processes.

These studies have resulted in the isolation and identification of novel xylanases and compositions containing the same, that are useful in such processes. Accordingly, the invention is directed to a cell-free composition comprising at least one xylanase of *Chaetomium thermophilum* var. *thermophilum*, *Chaetomium thermophilum* var. *coprophilum*, *Chaetomium thermophilum* var. *dissitum* or *Chaetomium thermophilum*, especially wherein such species is the same species as that represented by CBS 733.95, CBS 732.95, CBS 731.95 and CBS 730.95, respectively.

The invention is further directed to compositions containing a purified xylanase of Chaetomium, wherein such xylanase has a molecular weight of about 54 kDa, 33 kDa, 30 kDa (dimeric 60 kDa) or 22 kDa or xylanases having equivalent properties or mixtures containing more than one such xylanase.

The invention is further directed to methods of treating plant biomass with the cell-free or purified enzyme preparations of the invention. Such uses include the enzyme aided bleaching of wood pulp and methods of modifying plant biomass, like uses as feed additive or in baking.

The invention is further directed to a method of treating plant biomass with a cell-free enzyme preparation that contains at least one xylanase of *Chaetomium thermophilum* var. *coprophilum*, especially wherein such species is the same species as that represented by CBS 732.95.

BRIEF DESCRIPTION OF THE FIGURES

Legends to figures

Figure 1:
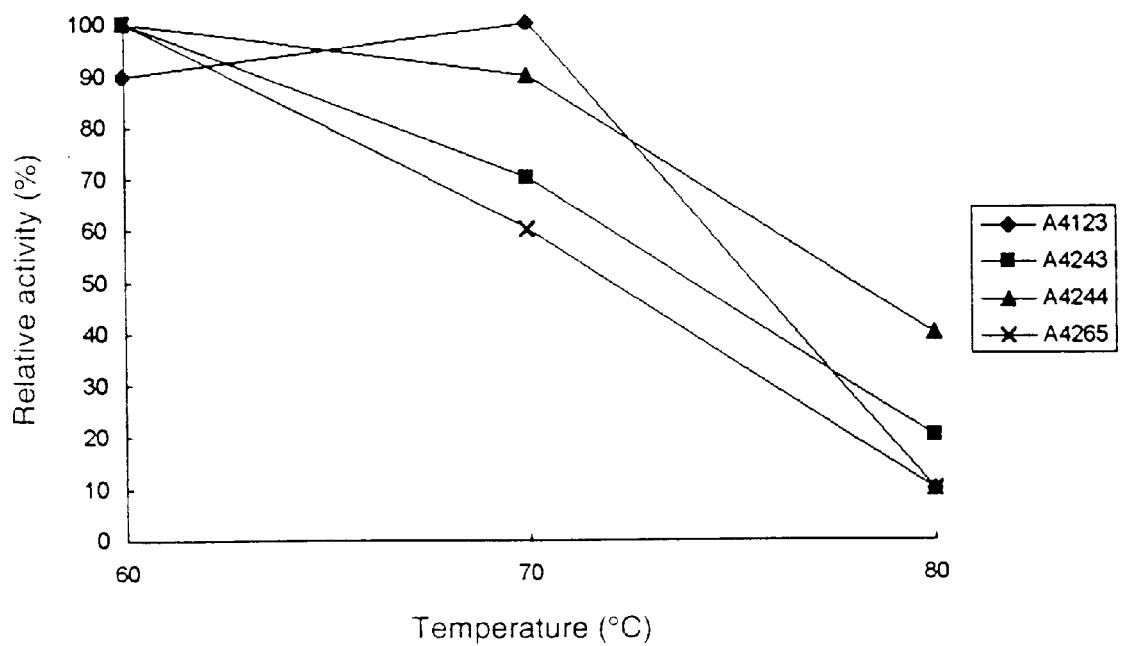
FIG. 1: Temperature profiles of the xylanase activity of the culture filtrates of ALKO4123, ALKO4243, ALKO4244, and ALKO4265 at pH 7.2 and 60 min incubation.

A: 22 kDa xylanase, B: 30 kDa xylanase, C: 33 kDa xylanase,

D: 54 kDa xylanase.

DETAILED DESCRIPTION OF THE PREFERRED EMBODIMENT

Deposits

*Chaetomium thermophilum* var. *thermophilum* ALKO4123 was deposited on Nov. 8, 1995 at the Centraalbureau Voor Schimmelcultures at Oosterstraat 1, Postbus 273 NL-3740 AG Baarn, The Netherlands, and assigned CBS 733.95. *Chaetomium thermophilum* var. *coprophilum* ALKO4243 was deposited on Nov. 8, 1995 at the Centraalbureau Voor Schimmelcultures at Oosterstraat 1, Postbus 273 NL-3740 AG Baarn, The Netherlands, and assigned as CBS 732.95.

*Chaetomium thermophilum* var. *dissitum* ALKO4244, was deposited on Nov. 8, 1995 at the Centraalbureau Voor Schimmelcultures at Oosterstraat 1, Postbus 273 NL-3740 AG Baarn, The Netherlands, and assigned as CBS 731.95.

ALKO4265, identified as *Chaetomium thermophilum* by the International Mycological Institute/Biosystem Services, was deposited on Nov. 8, 1995 at the Centraalbureau Voor Schimmelcultures at Oosterstraat 1, Postbus 273 NL-3740 AG Baarn, The Netherlands, and assigned CBS 730.95.

Definitions

In order to provide a clearer and consistent understanding of the specification and claims, including the scope to be given such terms, the following definitions are provided.

Xylanase. As used herein, a xylanase is a hemicellulase that cuts the β-1,4 bonds within the xylosic chain of xylan, (xylan is a polymer of D-xylose residues that are joined through β-1,4 linkages). Xylanase activity is synonymous with xylanolytic activity.

By an amino acid sequence that is an "equivalent" of a specific amino acid sequence is meant an amino acid sequence that is not identical to the specific amino acid sequence, but rather contains at least some amino acid changes (deletion, substitutions, inversions, insertions, etc) that do not essentially affect the biological activity of the protein as compared to a similar activity of the specific amino acid sequence, when used for a desired purpose. Preferably, an "equivalent" amino acid sequence contains at least 80% homology at the amino acid level to the specific amino acid sequence, most preferably at least 90% and in an especially highly preferable embodiment, at least 95% homology, at the amino acid level.

Enzyme preparation. By "enzyme preparation" is meant a composition containing enzymes that have been extracted from (either partially or completely purified from) a microbe or the medium used to grow such microbe. "Extractedfrom" means any method by which the desired enzymes are separated from the cellular mass and includes breaking cells and also simply removing the culture medium from spent cells. Therefore, the term "enzyme preparation" includes compositions containing medium previously used to culture a desired microbe(s) and any enzymes which the microbe(s) has secreted into such medium during the culture.

Enzyme-aided bleaching. By "enzyme-aided bleaching" is meant the extraction of lignin from cellulose pulp after the action of hemicellulose degrading enzymes with or without lignin degrading enzymes. Removal of the lignin may be restricted by hemicelluloses either physically (through reprecipitation onto the fiber surface during cooking) or chemically (through lignin-carbohydrate complexes). The hemicellulase activity partially degrades the hemicellulose, which enhances the extractability of lignins by conventional bleaching chemicals (like chlorine, chlorine dioxide. peroxide, etc.) (Viikari et al., "Bleaching with Enzymes" in *Biotechnology in the Pulp and Paper Industry*, Proc. 3rd Int. Conf., Stockholm, pp. 67–69 (1986); Viikari et al., "Applications of Enzymes in Bleaching" in *Proc. 4th Int. Symp. Wood and Pulping Chemistry*, Paris, Vol. 1, pp. 151–154 (1987); Kantelinen et al., "Hemicellulases and their Potential Role in Bleaching" in *International Pulp Bleaching Conference, Tappi Proceedings*, pp. 1–9 (1988)). The advantage of this improved bleachability is a lower consumption of bleaching chemicals and lower environmental loads or higher final brightness values.

Identification and Isolation of Chaetomium xylanases

Thermostable xylanases have been characterized from *Chaetomium thermophilum*. It has been found that strains of Chaetomium, and especially *Chaetomium thermophilum*, express and secrete thermostable xylanases that are useful e.g. in feed and baking as well as pulp and paper industry. These thermostable xylanases are useful in impure forms such as in enzyme compositions that contain, or essentially are, the spent culture medium from growth of the organism. For example, the xylanase activity in enzyme compositions containing the spent culture medium of *Chaetomium thermophilum* var. *thermophilum*, ALKO4123, was maximumly active at 70° C. In another example, the xylanase activity in enzyme compositions containing the spent culture medium of *Chaetomium thermophilum* var. *coprophilum*, ALKO4243, was maximumly active at 60° C. In another example, the xylanase activity in enzyme compositions containing the spent culture medium of *Chaetomium thermophilum* var. *dissitum*, ALKO4244, was maximumly active at 60° C. In a further another example, the xylanase activity in enzyme compositions containing the spent culture medium of *Chaetomium thermophilum*, ALKO4265, was maximumly active at 60° C.

In addition to the identification of useful enzyme compositions, four novel xylanases have been purified from the spent culture medium of *Chaetomium thermophilum*, ALKO4265. The molecular weights of these xylanases as determined by SDS-PAGE are about 22 kDa, 30 kDa, 33 kDa and 54 kDa. The accuracy of the SDS-PAGE molecular weight determination is about ten percent, leading to an estimation of about 22 kDa±2.2 kDa, 30 kDa±3.0 kDa, 33 kDa±3.3 kDa and 54 kDa±5.4 kDa, respectively. Possible glycosylation of these xylanases may cause wider variability in the molecular weights than the above mentioned values. The 30 kDa xylanase is probably dimeric in its native state as judged from molecular weight determinations by gelexclusion chromatography. Each of these xylanases has an alkaline pI as determined by chromatofocusing. The accuracy of the pI determination method is about 0.3 pH units. Each of these xylanases have a pH optimum and thermostability that are desirable for the enzyme-aided bleaching of wood pulp.

The 54 kDa, pI 8.9, xylanase shoved maximum activity at pH 6.2 and 80° C. in the pH range 6.2 to 7.9 and temperature range of 60 to 80° C.

The 33 kDa, pI 8.3, xylanase shoved maximum activity at pH 5.2 and 70° C. in the pH range 5.2 to 7.9 and temperature range of 50 to 80° C.

Surprisingly, both the 54 kDa and the 33 kDa xylanases of the invention are more thermostable at pH 7.2 in purified form than is the spent culture medium of the native host that secretes these enzymes.

The 30 kDa, pI 8.7, xylanase shoved maximum activity between pH 5.2–6.2 and 70° C. in the pH range 5.2 to 7.9 and temperature range of 50 to 80° C.

The 22 kDa, pI 9.3, xylanase shoved maximum activity at pH 6.2 and 60° C. in the pH range 5.2 to 7.9 and temperature range of 50 to 80° C.

Purification of a desired xylanase activity from a Chaetomium host of the invention is exemplified with ALKO4265. The four xylanases (22, 30, 33 and 54 kDa) are purified from spent culture medium by passage through a series of chromatographic columns. For example, Phenyl-Sepharose 6FF can be used to separate xylanase activities in culture medium into different pools.

The present invention comprehends a method for chemically treating plant biomass under conditions of high temperature of 50–80° C. and pH 5–8, and especially 60–70° C., pH 6–7 and most preferably 70° C. and pH 7 for a desired time, such as, for example, one hour. In a preferred embodiment, plant biomass or pulp is treated with xylanases that are able to hydrolyze xylan chains in lignocellulosic material at neutral or moderately alkaline pH and high temperature (above 60° C.) followed by bleaching of the pulp with conventional bleaching chemicals (like chlorine, chloride dioxid, peroxide, etc.).

Plant biomass is a composite material consisting primarily of a matrix of cellulose, hemicellulose, and lignin. Removal of the lignin component is desirable during the manufacture of paper pulp because of its brown color and tendency to reduce the strength of the paper product. Many processes have been developed for the removal of lignin. Typically, the wood pulp is treated with chlorine or other chemicals in order to remove the lignin component and provide for a brightened pulp. However, the toxic by-products of this chemical treatment negatively impact upon the health and stability of the environment into which they are released. Consequently there is a great need for developing alternative, more environmentally protective techniques to achieve pulp bleaching.

In a preferred embodiment, the process of the invention is carried out in vitro in the hemicellulose-containing pulp. The process involves placing the enzyme preparation, culture medium, or concentrated mixture containing xylanase into contact with the wood pulp. Routine calculations enable those in the art to determine the optimum treatment time depending upon the result desired, the concentration and specific activity of the xylanase enzyme used, the type and concentration of pulp used, pH and temperature of the wood pulp, and other parameter variables.

The method of the present invention may be applied alone or as a supplement to other treatments that reduce the lignin content of wood pulp, increase its drainability and/or decrease its water retention. In a preferred embodiment, the present invention is used to enhance bleachability of the wood pulp by treatment of chemical pulps, i.e., those pulps containing lignin that has been chemically modified through chemical treatment.

In a preferred embodiment, the xylanases present in the enzyme compositions of the invention and used in the methods of the invention are preferably those of Chaetomium, and especially *Chaetomium thermophilum*, and in an especially preferred embodiment, one or more of the purified 54 kDa, 33 kDa, 30 kDa or 22 kDa enzymes are used in the composition.

Therefore, according to the invention, there are provided enzyme compositions useful in feed and baking industry and for pulp and paper processing e.g. enzyme-aided bleaching. For bleaching, the enzyme preparations of the invention are preferably partially or completely deficient in cellulolytic activity (that is, in the ability to completely degrade cellulose to glucose) and enriched in xylanases desirable for pulp and paper processing. Such cellulolytic activity deficient preparations, and the making of same by recombinant DNA methods, are described in U.S. Pat. No. 5,298,405, incorporated herein by reference.

When used to treat plant pulp, the enzyme preparations of the invention may be utilized with any or all the usual bleaching chemicals, such as chlorine dioxide, hydrogen peroxide, ozone, oxygen, sodium hydroxide, etc. The dosage, pH, temperature, and time of enzyme treatment can all be easily varied so as to provide for maximum effectiveness of the treatment. For example, the pH may range from about pH 5 to about pH 8, the temperature may range from about 50° C. to about 80° C., the time of treatment with the enzyme preparation from about 0.5 hour to about 24 hours, and the dosage from about 20 to about 200 nkat/g of pulp dry matter. Enzyme treatment can be added to various bleaching processes, that are sequences of successive chemical treatment stages. Typical bleaching processes are: 1) elemental chlorine containing sequences that can be represented by e.g. a sequence of X(C/D)EDED, where X indicates a treatment with an enzyme, such as an enzyme of the invention, C/D indicates combined treatment with elemental chlorine (C) and chlorine dioxide (D), E indicates an alkaline extraction and D indicates chlorine dioxide treatment; 2) elemental chlorine-free (ECF) sequences that can be represented by e.g. a sequence of XDEDED (the two D steps used in the XDED sequence shown in Table 2 are named $D_0$ and $D_1$); 3) total chlorine-free (TCF) sequences that can be represented by e.g. a sequence of XQPPP, where Q stands for chelation, i.e. metal removal stage, and P indicates a hydrogen peroxide treatment (PPP indicates three successive peroxide stages, $P_1P_2P_3$). Typical TCF sequences also include different other stages, like different extraction stages (E, EO, EOP), ozone (Z), oxygen (O), pressurized peroxide stage (OP) etc.

The enzyme preparations of the invention satisfy the requirements of specific needs in various applications in the pulp and paper industry, including the debarking of logs and refining of wood to reduce energy demands in mechanical pulp production. In pulp beating, the enzyme preparations of the invention can be used to increase external fibrillation, and enhanced of facilitate swelling of the pulp fibers, and thus improve the paper making properties of the fibers. The xylanases present in the enzyme preparation of the invention can also be used to improve pulp drainability and/or decrease water retention.

The enzyme preparations of the invention may also be used as feed additives, and thus improve animal growth rate and feed conversion. When used in baking, improvement of the dough and the bread characteristics may be obtained.

To obtain the enzyme preparations of the invention, the native hosts described above are cultivated under suitable conditions. The desired enzymes are secreted from the hosts into the culture medium, and the enzyme preparation is recovered from said culture medium by methods known in the art. The enzyme preparation may include the native organism, or the native organism may be removed from the culture medium by application of methods well known in the art. The enzyme preparations of the invention may be provided as a liquid or as a solid, for example, in a dried powder or granular or liquid form, especially nondusting granules, or stabilized liquid, or the enzyme preparation may be otherwise concentrated or stabilized for storage or use. It is envisioned that enzyme preparations containing one or more of the xylanases of the invention can be further enriched or made partially or completely deficient in specific enzymatic activities, so as to satisfy the requirements of a specific utility in various applications e.g. in feed, baking and pulp and paper industry. A mixture of enzyme activities secreted by a host and especially a fungus, can be chosen to be advantageous in a particular industrial application, for example enzyme-aided bleaching.

The enzyme preparations of the invention can be adjusted to satisfy the requirements of specific needs in various applications in the feed, baking and pulp and paper industry.

Blends may be prepared with other macromolecules that are not all secreated from the same host (for example, other enzymes such as endoglucanases, proteases, lipases, peroxidases, oxidases, amylases or cellobiohydrolases) or chemicals that may enhance the performance, stability, or buffering of the desired enzyme preparation. Non-dusting granules may be coated. Liquid enzyme preparations can be stabilized by adding a polyol such as propylene glycol, a sugar or sugar alcohol, lactic acid or boric acid, according to established methods.

It is an advantage of the invention that the enzyme preparations of the invention may be utilized directly from the culture medium with no further purification.

However, if desired, the xylanase of the invention may be further purified in accordance with conventional conditions, such as extraction, precipitation, chromatography, affinity chromatography, electrophoresis, or the like. As exemplified herein, purification of the 54 kDa and the 33 kDa results in an enzyme compositions that surprisingly have enhanced thermostability when compared to the culture medium from which the enzyme was derived. Accordingly, when thermostability is especially desired, it is an advantage of the invention to use purified preparations of the 54 kDa and/or the 33 kDa enzymes in the enzyme composition.

The invention is described in more detail in the following examples, These examples show only a few concrete applications of the invention. It is self evident for one skilled in the art to create several similar applications. Hence the examples should not be interpreted to narrow the scope of the invention only to clarify the use of the invention.

EXAMPLES

Example 1

Cultivation of *Chaetomium thermophile* ALKO4123, ALKO4243, ALKO4244 and ALKO4265

*Chaetomium thermophilum* var. *thermophilum* ALKO4123 (CBS 733.95), *Chaetomium thermophilum* var. *coprophilum* ALKO4243 (CBS 732.95), *Chaetomium thermophilum* var. *dissitum* ALKO4244 (CBS 731.95) and ALKO4265 (CBS 730.95, identified as *Chaetomium thermophilum* by the International Mycological Institute/Biosystem Services) were maintained on sporulation agar (ATCC medium 5).

For the bleaching tests ALKO4244 was cultivated in 750 ml of the following medium: 1.5% distiller's spent grain, 0.2% soy bean meal, 0.15% $(NH_4)_2HPO_4$, 0.2% $KH_2PO_4$, 0.05% $MgSO_4 \times 7H_2O$, 0.05% NaCl, 0.1% $CaCO_3$, 0.03% $FeSO_4 \times 7H_2O$, 0.001% $MnSO_4$, pH was adjusted to 6.5.

ALKO4123, ALKO4243 and ALKO4265 were cultivated each in 750 ml of the following medium: 0.6% Solka floc, 0.6% distiller's spent grain, 0.3% oat spelt xylan, 0.2% $CaCO_3$, 0.15% soy bean meal, 0.15% $(NH_4)_2SO_4$, 0.1% barley bran, 0.05% $KH_2PO_4$ 0.05% $MgSO_4 \times 7H_2O$, 0.05% NaCl, 0.05% trace element solution 1, 0.05% trace element solution 2, 0.03% $KNO_3$, pH was adjusted to 6.5. The trace element solution 1 contained 1.6 g/l $MnSO_4$, 3.45 g/l $ZnSO_4 \times 7H_2O$, 2 g/l $CoCl_2 \times 6H_2O$. The trace element solution 2 contained 5 g/l $FeSO_4 \times 7H_2O$.

All cultivations were incubated at 45° C. for 3 days in a rotary shaker at 250 rpm.

For purification of xylanases of ALKO4265, 1 1 fermenter cultivations (Biostat M, B. Braun, Melsungen, Germany) were performed in a cultivation medium containing 0.3% Roth xylan, 3% soy bean meal, 4% whey, 0.5% $(NH_4)_2SO_4$, 0.1% NaCl, 0.5% $KH_2PO_4$, 0.2% $CaCO_3$, 0.05% trace element 1 (see above), 0.05% trace element 2 (see above), 0.05 % $MgSO_4$. A 10% inoculum of a shake flask cultivation was used. The pH was maintained at 6.6±0.4 by addition of ammonia (12.5%) and phosphoric acid (17%). The fermenter was stirred at 700 rpm and the air flow was 1 liter/min. The growth temperature was 45° C. and growth time 1–3 days.

Example 2

Temperature Profiles of the Culture Filtrates of *Chaetomium thermophilum*

The culture filtrate of ALKO4123, ALKO4243, ALKO4244 and ALKO4265 were tested for thermal stability by incubating samples at 60, 70 and 80° C. at pH 7.2 for 60 min with Roth (No. 7500) birch wood xylan. The released xylose was measured as in the xylanase activity measurement method described by Bailey,M et al., *J.Biotechnol.* 23:257–270 (1992). The results are shown in FIG. 1. ALKO4123 showed maximum activity at 70° C., while the other three culture filtrates showed maximum activity at 60° C.

Example 3

Experiments Using *Chaetomium thermophilum* Culture filtrates in One Stage Peroxide Bleaching Bleaching experiments were done to determine the usefulness of *Chaetomium thermophilum* var. *thermophilum* CBS 733.95 (ALKO4123), *C. thermophilum* var. *dissitum* CBS 731.95 (ALKO4244) and *C. thermophilum* CBS 730.95 (ALKO4265) xylanase activity containing culture filtrates in one-stage peroxide bleaching.

Culture filtrates (Example 1) from growth of *C. thermophilum* ALKO4123, ALKO4244 and ALKO4265 were added to Finnish oxygen-delignified softwood kraft pulp (kappa number 16, brightness 33%) in the amount of 100 nkat/g of pulp dry matter. Xylanase activity expressed as nkat was measured according to Bailey et al., J. Biotechnol. 23:257–270 (1992) by using Roth birch wood xylan (no. 7500) as substrate at 70° C. and pH 7.0 with a 60 minutes incubation time. The enzyme treatments were done at 70° C. and pH 7 for one hour. Reference pulp was treated in the same way but without enzyme addition.

Bleaching was performed with $QP_1$ sequence. The chelation stage (Q) was performed by adding EDTA to 0.2% of pulp dry matter and it was carried out at 3% pulp consistency. Bleaching chemicals in the hydrogen peroxide stage ($P_1$) were the following: 3% $H_2O_2$, 3% NaOH, 0.2% diethylene triaminepentaacetic acid (DTPA) and 0.5% $MgSO_4$. Conditions of the Q and $P_1$ stages as well as the results of the bleaching experiments are shown in Table 1(a and b).

TABLE 1a

|  | Reference | ALKO4123 |
|---|---|---|
| Enzyme treatment |  |  |
| Consistency, % | 3.5 | 3.5 |
| Retention time, hours | 1 | 1 |
| Enzyme dosage, nkat/g | 0 | 100 |
| Temperature, ° C., start/end | 72169 | 68/68 |
| pH, start/end | 7.3/7.3 | 7.3/7.4 |
| Q-stage |  |  |
| Consistency, % | 3 | 3 |
| Retention time, hours | 1 | 1 |
| Temperature at the end, ° C. | 63 | 62 |
| pH at the end | 4.9 | 4.9 |
| EDTA, % of dry matter | 0.2 | 0.2 |
| $P_1$-stage |  |  |
| Consistency, % | 10 | 10 |
| Retention time, hours | 3 | 3 |
| Temperature, ° C. | 80 | 80 |
| pH, start/end | 11/10.5 | 11.4/11.3 |
| Peroxide dosage, % | 3 | 3 |
| Peroxide consumed, % | 2.9 | 2.9 |
| Brightness, % | 57.1 | 58.8 |
| Kappa number | 9.7 | 8.5 |

TABLE 1b

|  | Reference | ALKO4244 | ALKO4265 |
|---|---|---|---|
| Enzyme treatment |  |  |  |
| Consistency, % | 3.5 | 3.5 | 3.5 |

TABLE 1b-continued

|  | Reference | ALKO4244 | ALKO4265 |
|---|---|---|---|
| Retention time, hours | 1 | 1 | 1 |
| Enzyme dosage, nkat/g | 0 | 100 | 100 |
| Temperature, °C., start/end | 67/70 | 70/72 | 70/71 |
| pH, start/end | 7.0/6.9 | 6.9/6.9 | 7.1/7.0 |
| Q-stage |  |  |  |
| Consistency, % | 3 | 3 | 3 |
| Retention time, hours | 1 | 1 | 1 |
| Temperature at the end, °C. | 57 | 60 | 58 |
| pH at the end | 5.3 | 5.4 | 5.2 |
| EDTA, % of dry matter | 0.2 | 0.2 | 0.2 |
| $P_1$-stage |  |  |  |
| Consistency, % | 10 | 10 | 10 |
| Retention time, hours | 3 | 3 | 3 |
| Temperature, °C. | 80 | 80 | 80 |
| pH, start/end | 11.7/10.8 | 11.6/10.7 | 11.7/10.7 |
| Peroxide dosage, % | 3 | 3 | 3 |
| Peroxide consumed, % | 2.6 | 2.6 | 2.6 |
| Brightness, % | 65.2 | 67.7 | 66.7 |
| Kappa number | 8.3 | 8.0 | 7.4 |

As can be seen in Table 1(a and b) the use of xylanase activity containing culture filtrates of *C. thermophilum* ALKO4123, ALKO4244 and ALKO4265 as pretreatment in the one-stage peroxide bleaching clearly increased the brightness obtained without increasing the amount of hydrogen peroxide that was consumed. Also lignin content of pulps was decreased as evidenced by the reduction of kappa number.

Example 4

Experiments Using *Chaetomium thermophilum* Culture Filtrates in Chlorine Dioxide (ECF) Bleaching and Three Stage Peroxide (TCF) Bleaching Bleaching experiments were done to determine the usefulness of *Chaetomium thermophilum* CBS 730.95 (ALKO4265) and CBS 731.95 (ALKO4244) xylanase activity containing culture filtrates both in ECF (elementary chlorine free) and in TCF (totally chlorine free) bleaching of pulp.

ECF Bleaching

Culture filtrates (Example 1) were added to Finnish oxygen-delignified softwood kraft pulp (kappa number 15.5, viscosity 900 ml/g, brightness 43.5%) in the amount of 100 nkat/g of pulp dry matter. Xylanase activity expressed as nkat was measured according to Bailey, M. et al., J. Biotechnol. 23:257–270 (1992) by using Roth (no. 7500) birch wood xylan as substrate at 70° C., pH 7.0 with a 5 minutes incubation time. The enzyme treatments were done at 70° C., pH 7 for one hour. Reference pulp was kept under the same conditions without enzyme addition. After the enzyme treatments bleaching was performed with $D_0E\,D_1$ sequence, where $D_0$ stands for the first chlorine dioxide stage, E alkali extraction and $D_1$ the second chlorine dioxide stage. Bleaching conditions and results are shown in Table 2.

TABLE 2

|  | Reference | ALKO4244 | ALKO4265 |
|---|---|---|---|
| Enzyme treatment |  |  |  |
| Consistency, % | 3 | 3 | 3 |

TABLE 2-continued

|  | Reference | ALKO4244 | ALKO4265 |
|---|---|---|---|
| Retention time, hours | 1 | 1 | 1 |
| Enzyme dosage, nkat/g | 0 | 100 | 100 |
| Temperature, °C. | 70 | 70 | 70 |
| pH, start/end | 7.0/7.4 | 6.9/7.2 | 6.9/7.1 |
| $D_0$-stage |  |  |  |
| Consistency, % | 3 | 3 | 3 |
| Retention time, hours | 1 | 1 | 1 |
| Temperature, °C. | 60 | 60 | 60 |
| $ClO_2$-dosage, % | 2.3 | 2.3 | 2.3 |
| $ClO_2$, consumed, % | 2.3 | 2.3 | 2.3 |
| pH at the end | 2.5 | 2.5 | 2.5 |
| E-stage |  |  |  |
| Consistency, % | 10 | 10 | 10 |
| Retention time, hours | 1 | 1 |  |
| Temperature, °C. | 70 | 70 | 70 |
| NaOH, % | 1.5 | 1.5 |  |
| pH at the end | 10.8 | 10.8 | 10.8 |
| Brightness, % | 58.8 | 62.3 | 62.5 |
| Kappa number | 6.6 | 5.4 | 5.4 |
| Viscosity, ml/g | 860 | 850 | 800 |
| $D_1$-stage |  |  |  |
| Consistency, % | 10 | 1.0 | 10 |
| Retention time, hours | 3 | 3 | 3 |
| Temperature, °C. | 60 | 60 | 60 |
| $ClO_2$-dosage, % | 2.0 | 2.0 | 2.0 |
| $ClO_2$, consumed, % | 2.0 | 2.0 | 2.0 |
| pH at the end | 3.4 | 3.2 | 3.2 |
| Brightness, % | 79.1 | 82.4 | 82.5 |
| Kappa number | 2.1 | 1.5 | 1.5 |

As can be seen in Table 2, the enzyme pretreatments enhanced lignin removal, which is evidenced by the reduction of kappa numbers. Also brightness values of the final pulps were higher compared with the reference although chlorine dioxide consumption was not increased. Reduction in viscosity with ALKO4265 was due to cellulase activity present in the enzyme preparation.

TCF Bleaching

Culture filtrates (Example 1) from growth of Chaetomium thermophilum ALKO4244 and ALKO4265 were added to Finnish oxygen-delignified softwood kraft pulp (kappa number 16, brightness 33%) in the amount of 100 nkat/g of pulp dry matter. Xylanase activity expressed as nkat was measured according to Bailey et al., J. Biotechnol. 23:257–270 (1992) by using Roth (no. 7500) birch wood xylan as substrate at 70° C., pH 7.0 with a 60 minutes incubation time. The enzyme treatments were done at 70° C., pH 7 for one hour. Reference pulp was treated in the same way but without enzyme addition. Bleaching was performed with $QP_1P_2P_3$ sequence. The chelation stage (Q) was performed by adding EDTA to 0.2% of pulp dry matter and it was carried out at 3% pulp consistency. The three successive hydrogen peroxide stages ($P_1P_2P_3$) were carried out the same way except that after each stage, one-third of the pulp was removed for testing. Bleaching chemicals in P stages were the following: 3% $H_2O_2$, 3% NaOH, 0.2% diethylene triaminepentaacetic acid (DTPA) and 0.5% $MgSO_4$. Conditions of the Q and P stages as well as the results of the bleaching experiment are shown in Table 3.

TABLE 3

|  | Reference | ALKO4244 | ALKO4265 |
|---|---|---|---|
| Enzyme treatment |  |  |  |

TABLE 3-continued

|  | Reference | ALKO4244 | ALKO4265 |
|---|---|---|---|
| Consistency, % | 3.5 | 3.5 | 3.5 |
| Retention time, hours | 1 | 1 | 1 |
| Enzyme dosage, nkat/g | 0 | 100 | 100 |
| Temperature, ° C. | 68 | 68 | 68 |
| pH, start/end | 7.3/7.3 | 7.1/7.0 | 7.0/6.9 |
| Q-stage | | | |
| Consistency, % | 3 | 3 | 3 |
| Retention time, hours | 1 | 1 | 1 |
| Temperature at the end, ° C. | 56 | 58 | 58 |
| pH at the end | 5.4 | 5.7 | 5.3 |
| EDTA, % of dry matter | 0.2 | 0.2 | 0.2 |
| $P_1$-stage | | | |
| Consistency, % | 10 | 10 | 10 |
| Retention time, hours | 3.5 | 3.5 | 3.5 |
| Temperature, ° C. | 80 | 80 | 80 |
| pH, start/end | 11.2/10.7 | 11.4/10.8 | 11.4/10.7 |
| Peroxide dosage, % | 3 | 3 | 3 |
| Peroxide consumed, % | 2.3 | 2.3 | 2.4 |
| Brightness, % | 61.2 | 62.7 | 62.5 |
| Kappa number | 9.6 | 9.3 | 9.0 |
| $P_2$-stage | | | |
| Consistency, % | 10 | 10 | 10 |
| Retention time, hours | 3 | 3 | 3 |
| Temperature, ° C. | 80 | 80 | 80 |
| pH, start/end | 11.4/11.2 | 11.3/11.0 | 11.3/11.0 |
| Peroxide dosage, % | 3 | 3 | 3 |
| Peroxide consumed, % | 2.3 | 2.2 | 2.2 |
| Brightness, % | 67.7 | 69.5 | 69.4 |
| Kappa number | 8.5 | 7.8 | 8.0 |
| $P_3$-stage | | | |
| Consistency, % | 10 | 10 | 10 |
| Retention time, hours | 3 | 3 | 3 |
| Temperature, ° C. | 80 | 80 | 80 |
| pH, start/end | 11.4/10.9 | 11.3/10.6 | 11.3/10.6 |
| Peroxide dosage, % | 3 | 3 | 3 |
| Peroxide consumed, % | 2.3 | 2.2 | 2.2 |
| Brightness, % | 73.6 | 74.7 | 74.6 |
| Kappa number | 7.6 | 6.8 | 6.7 |
| Viscosity, ml/g | 730 | 760 | 720 |
| Total peroxide consumption, % | 6.9 | 6.7 | 6.8 |

As can be seen in Table 3 the use of xylanase containing culture filtrates of *Chaetomium thermophilum* ALKO4244 and ALKO4265 as a pretreatment in the peroxide bleaching clearly increased the brightness obtained without increasing the amount of hydrogen peroxide that was consumed. Enzyme treatments did not affect the viscosity of the pulps.

Example 5

Purification of xylanases from *Chlaetomium thermophilum* ALKO4265

The culture filtrate of 1–3 days fermentations of ALKO4265 (Example 1) were used for purification purposes.

Determination of protein concentration

For protein concentration measurements, the standard Bio-Rad assay (based on the method of Bradford. M., *Analytical Biochemistry* 72:248–254 (1976)) standardized with gamma-globulin was used. During gel-exclusion chromatography runs, protein concentration was followed by measurements at $A_{280}$.

Activity measurements

During fermentations and enzyme purifications xylanase activity was measured according to Bailey, M. et al., *J.Biotechnol.* 23:257–270 (1992) by using Roth (No 7500 ) birch wood xylan as substrate at 60° C., pH 6.5 McIlvain's buffer with 5 min incubation. The activity is expressed as nkat.

Polyacrylamide gel electrophoresis (SDS-PAGE)

Polyacrylamide slab gels (12% or 14%) were run as described by Laemmli, U. K. *Nature* 227:680–685 (1970) in the presence of 0.1% sodium dodecyl sulphate and stained with Coomassie Brilliant Blue. Molecular mass standards (Bio-Rad, Low Range Prestained SDS-PAGE Standards) were used to estimate molecular masses of sample proteins.

Temperature and pH—profiles

Temperature and pH profiles were obtained by incubating samples at defined temperatures and pH, obtained by using McIlvains buffers, for 1 h with Roth (No. 7500) birch wood xylan as described in activity measurements.

Determination of pI

Chromatofocusing of purified xylanases was performed on a mono P column (0.5×20 cm, Pharmacia) equilibrated with 25 or 70 mM Tris-acetic acid pH 9.5 at 30 ml/h. Elution was accomplished with Polybuffer 96 (Pharmacia) diluted 1:10 with distilled water and adjusted to pH 6.2 with acetic acid. Fractions of 0.5 to 1 ml were collected and both the xylanase activity and pH of each fraction was measured. The pI estimates of the purified proteins are means of two separate runs.

Purification of xylanases from A4265

Approximately 900 ml of ALKO4265 culture filtrate was adjusted to pH 7.5 with 1M NaOH and HCl. Unless otherwise stated, samples were kept at +4° C. In order to run hydrophobic interaction chromatography, ammonium sulphate was added to a final concentration of 0.5M. Alternatively culture filtrate was adjusted to pH 7.5 and EDTA added to 1 mM concentration then precipitated with 45% (w/v) ammonium sulphate. The precipitate was separated by centrifugation at 10,000 g for 20 min. The precipitate was suspended in 20 mM Tris-HCl pH 7.5 containing 1 mM EDTA and ammonium sulphate was added to a final concentration of 0.5M.

Culture filtrate treated as above was applied on a Phenyl-Sepharose 6FF column (Pharmacia, 5 cm×12 cm) equilibrated at room temperature with 20 mM Tris-HCl buffer pH 7.5 containing 0.5M ammonium sulphate (buffer A). Elution was performed at 30 ml/min with a linear gradient of buffer A to buffer A without ammonium sulphate (buffer B) in 10 min. Elution with buffer B was continued for an additional 10 min followed by a linear gradient of buffer B to buffer B containing 60% ethylene glycol (buffer C) in 20 min. Elution with buffer C was prolonged for a further 10 min. Fractions of 10 ml were collected and assayed for xylanase activity and protein concentration.

Figure 2:
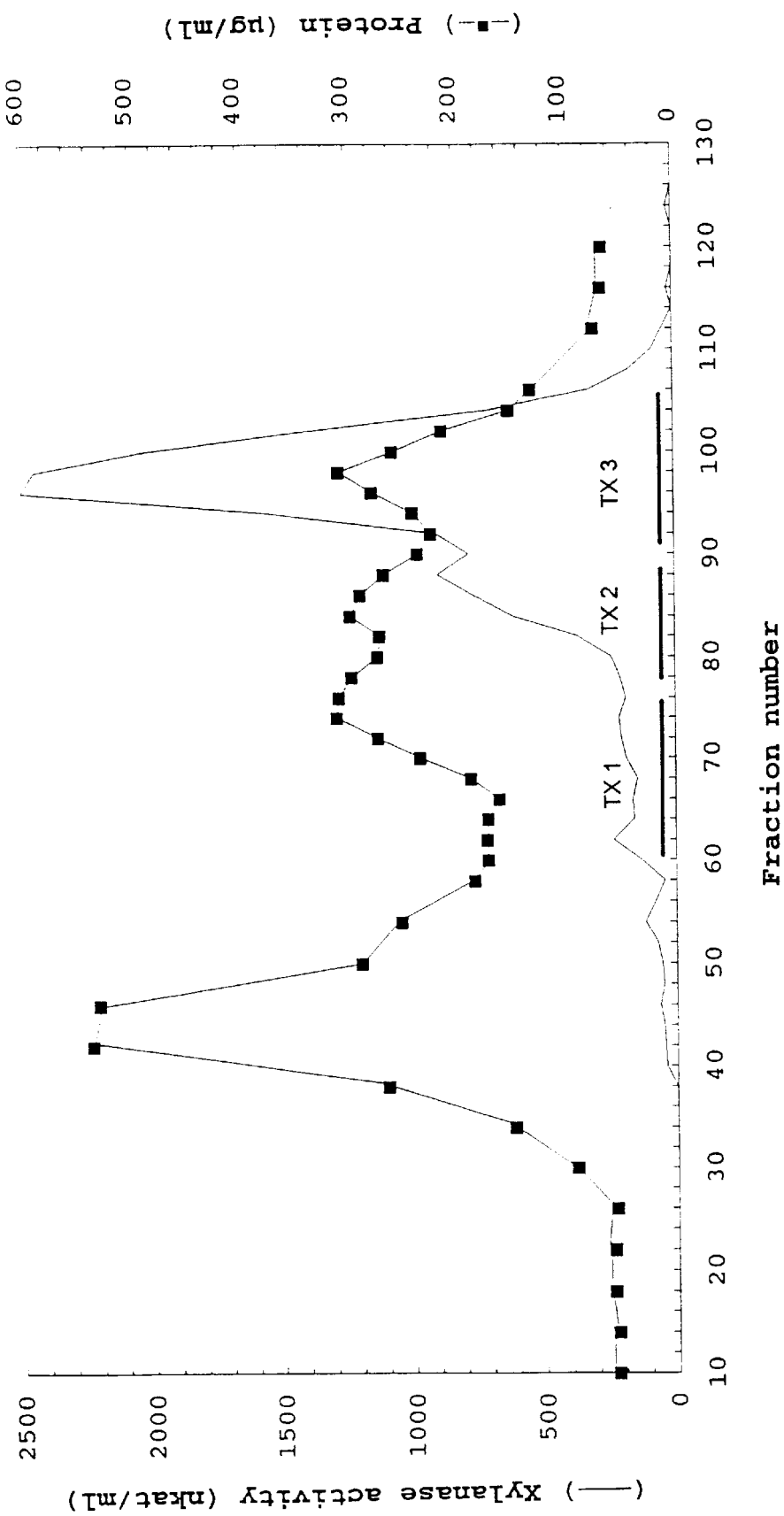
FIG. 2: The chromatogram of the Phenyl-Sepharose 6FF run of the ALKO4265 culture filtrate. Pools TX1, TX2, TX3 are indicated.
Figure 3A:
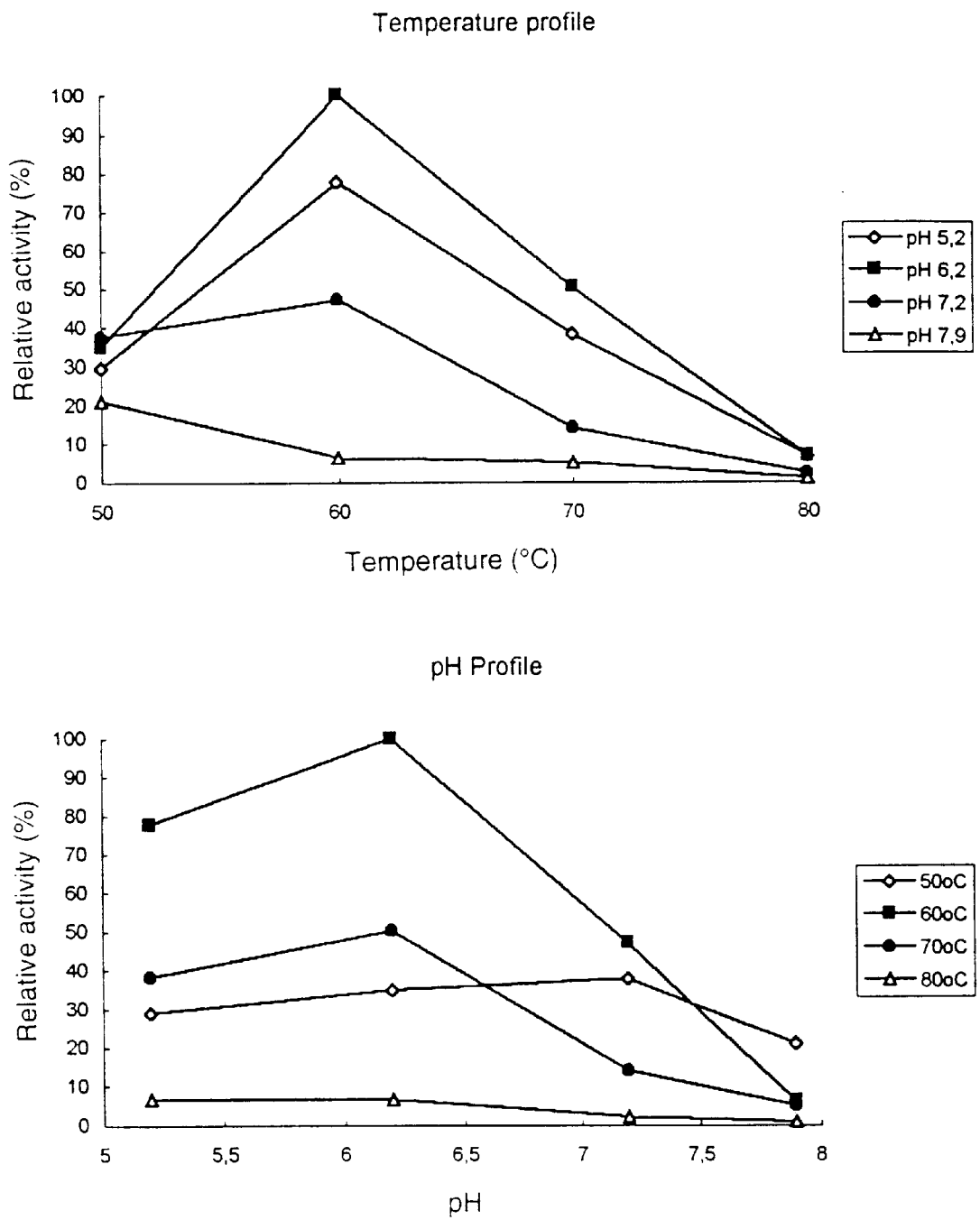
FIGS. 3A–3D: Temperature and pH profiles of the purified xylanases of ALKO4265. Incubation time 1 h.
Figure 3B:
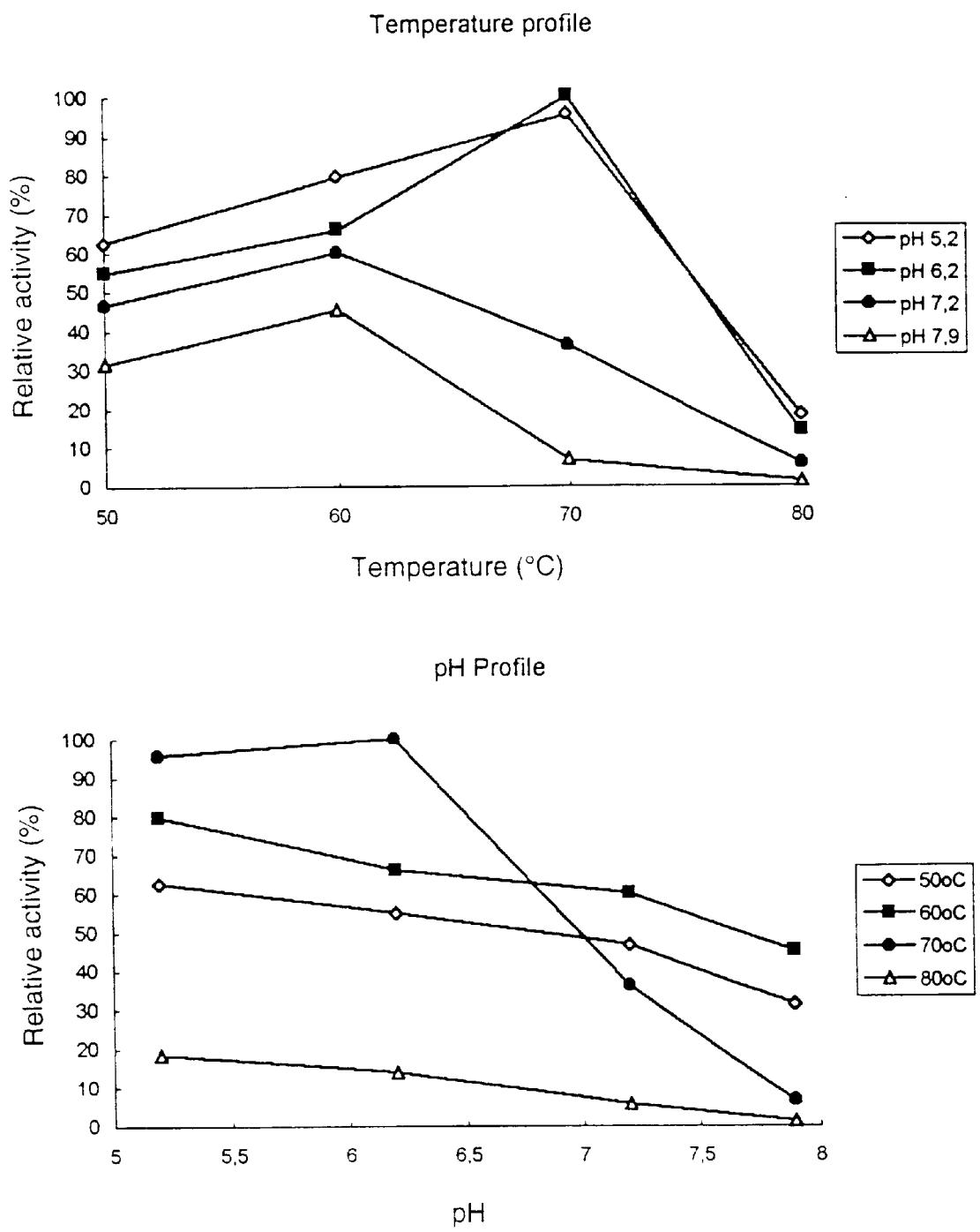
Figure 3C:
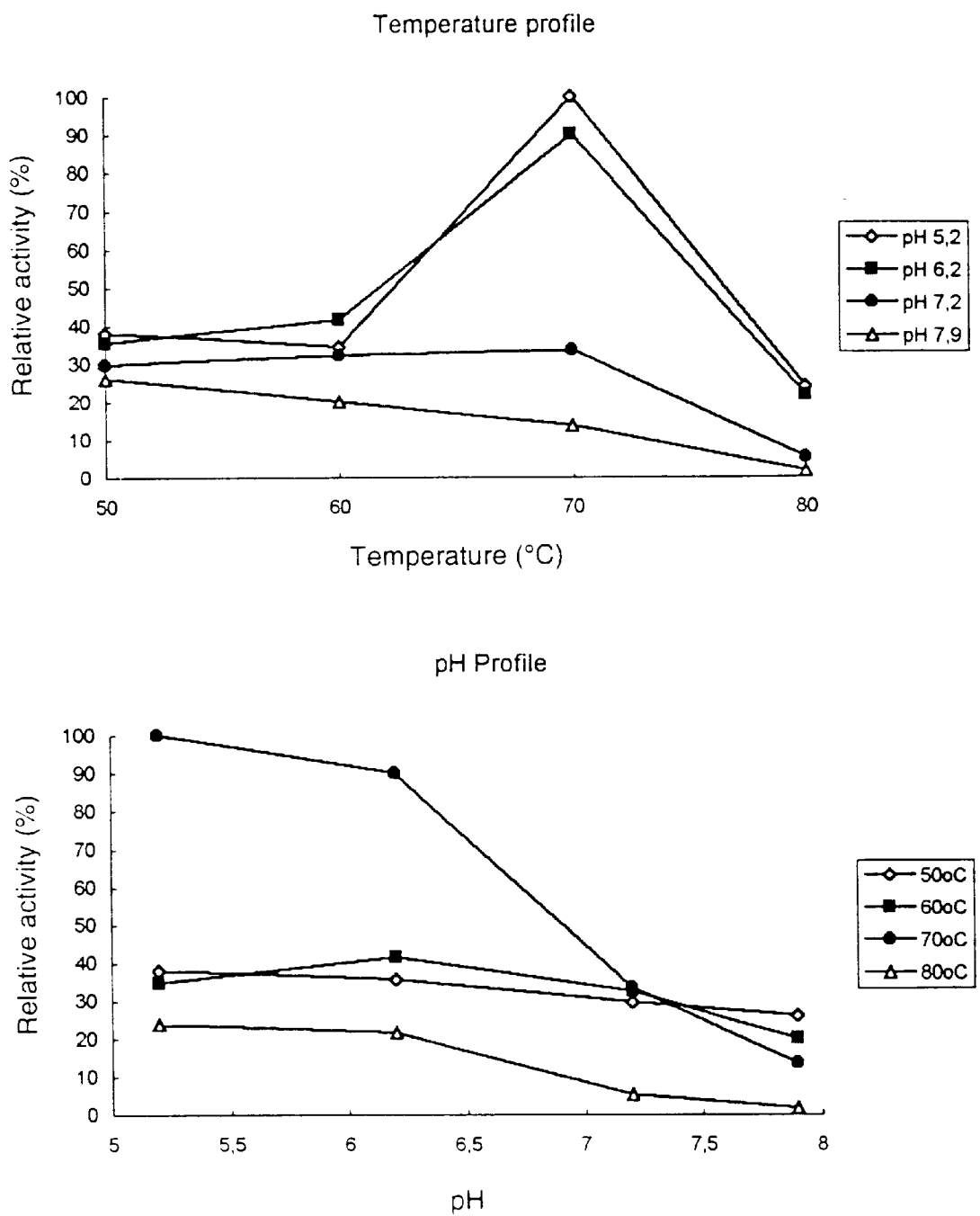
Figure 3D:
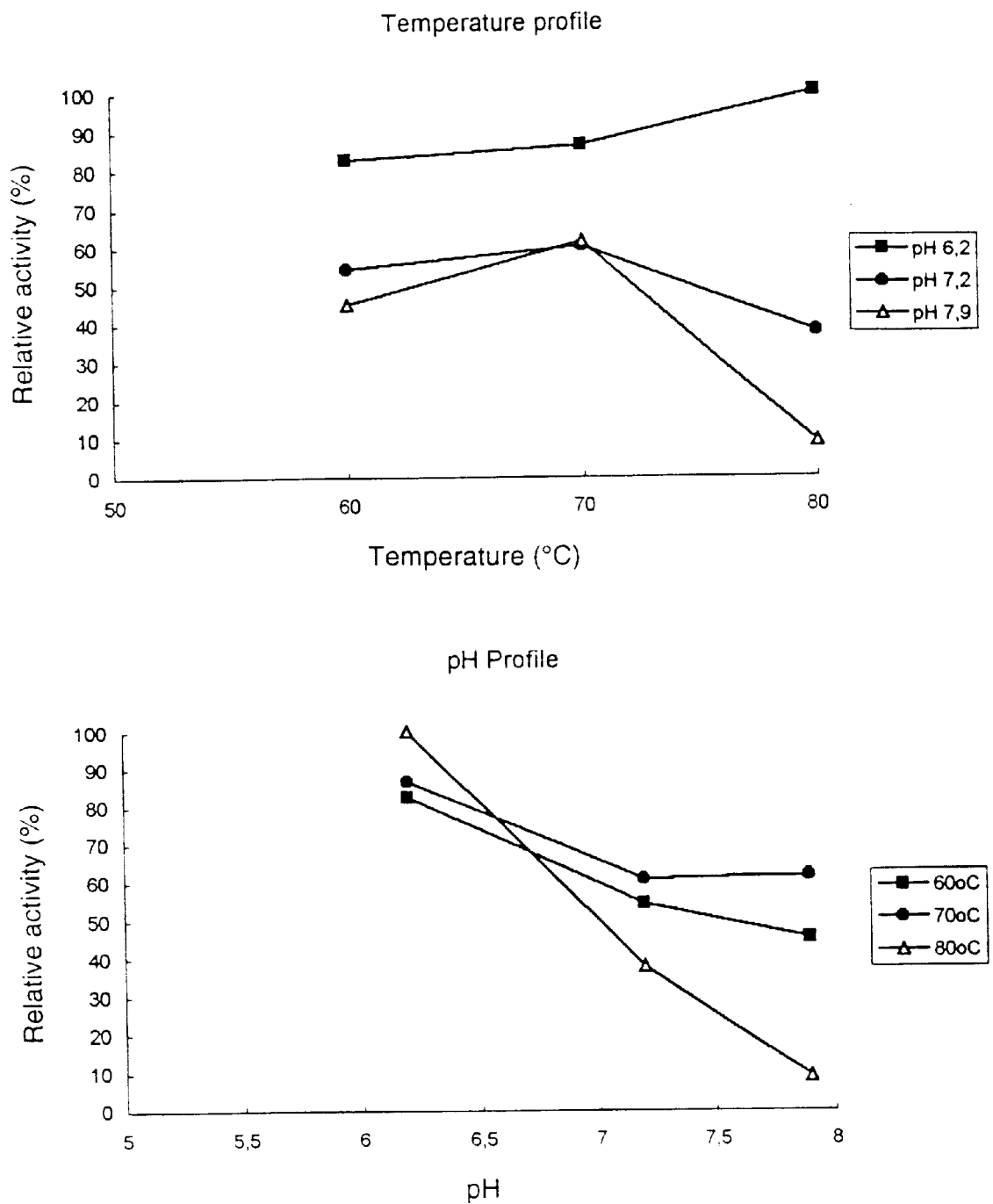

Three separate pools (see FIG. 2) containing xylanase activity were obtained from the Phenyl-Sepharose 6FF run. Pool TX1 eluted with approximately 20%, pool TX2 with 40% and pool TX3 with 60% ethylene glycol. Samples of each pool were concentrated with an Amicon concentrator (10 kDa cut off membranes). The concentration succeeded only with pool TX1, resulting in a 10 fold concentration and over 80% recovery of xylanase activity. Concentration of TX2 and TX3 resulted in only about 30 and 15% recoveries, respectively.

Further purification of pool TX1

Concentrated TX1 was run on a Superdex G-75 HiLoad column (Pharmacia, 2.6×60 cm) equilibrated at room temperature with 20 mM disodium hydrogen phosphate pH 8.6 containing 100 mM NaCl at 120 ml/h. Fractions of 6 ml were collected and assayed for xylanase activity. Two xylanase activity containing pools were obtained and run on SDS-PAGE.

The early eluting peek-pool, eluting close to the 68 kDa BSA used as standard in the Superdex G-75 run, contained a protein of approximately 30 kDa as estimated on SDS-PAGE. Thus this xylanase seems to be dimeric in its active form. The pI of this xylanase is 8.7 as determined by chromatofocusing.

The second, later eluting peek-pool contain mainly a protein of approximately 54 kDa. Since there was two main bands in this sample pool, an aliquot was further concentrated with a Centricon microconcentrator (10 kDa cut off) and run on a Superose 12 column equilibrated with 20 mM Tris-HCl pH 7.5 containing 100 mM NaCl at 30 ml/h. The xylanase activity containing fractions were pooled. A sample of this pool was run on SDS-PAGE. It showed a single band of approximately 54 kDa. Elution from the Superose 12 column indicated that the enzyme is monomeric in its active form. The pI of this 54 kDa xylanase, as determined by chromatofocusing, is 8.9.

Further purification of pools TX2 and TX3

Since the concentration of TX2 and TX3 on Amicon failed, both pools were concentrated by ammonium sulphate precipitation (45% w/v) after addition of EDTA to a final concentration of 1 mM. The precipitates were suspended in 20 mM Tris-HCL pH 7.5 and run on a Superdex G-75 column equilibrated with 20 mM Tris-HCl pH 7.5, containing 100 mM NaCl, at 120 ml/h. Fractions of 6 ml were collected. The xylanase activity containing fractions of both runs were pooled separately and assayed on SDS-PAGE.

The TX2 Superdex G-75 pool showed four main bands. Further purification was accomplished by concentrating an aliquot by using Centricon micro concentrators (10 kDa cut off) and running a Superose 12 column as above. The xylanase activity containing fractions were pooled and assayed on SDS-PAGE. Purified TX2 showed a protein of approximately 33 kDa. Elution from the Superose 12 column indicated that the xylanase is monomeric in its active form. A pI of 8.3 was estimated from chromatofocusing runs.

The TX3 Superdex G-75 pool showed a homogeneous 22 kDa band on SDS-PAGE and a pI of 9.3 as estimated by chromatofocusing. Also this enzyme is monomeric in its active form, as judged from its elution from the Superdex G-75 column.

Amino acid sequencing of the 22 kDa and 54 kDa xylanases

The 22 kDa band of a dried SDS-PAGE gel was cut out and subjected to Edman degradation in a gas-pulsed-liquid-phase sequencer (Kalkkinen & Tilgmann, *J. Prot. Chem.* 7: 242–243 (1988)). The 36 amino acid N-terminal sequence obtained is shown in Table 4 (24 kDa). A BLAST search (NCBI, National Center of Biological Information) revealed sequence identities to many xylanases. The highest identity scores were obtained for the putative N-terminal sequences of *Emericella nidulans* xyna and xynb (both 64% identity) and *Aspergillus kawachii* xynb (64% identity). The sequence identity to the N-terminal sequence of *Schizophyllum commune* xyna was 55%.

A sample of 54 kDa xylanase was subjected to enzymatic digestion with 2% (w/w) modified trypsin (Promega) in 1% ammonium bicarbonate for 3 hours at 37° C. The peptides obtained were separated by reversed-phase chromatography on a 0.21 cm×15 cm Spherisorb S5 (5 μm particle size; 30 nm pore size) column using a linear gradient of acetonitrile (3–100% in 100 min) in 0.1% trifluoroacetic acid at a flow rate of 200 μl/min. Selected peptides were subjected to Edman degradation as above. Two peptide sequences were obtained from the 54 kDa xylanase. The 15 amino acid peptide 54 kDaA (Table 4) shoved 67% identity to a internal sequence of *Clostridium thermocellum* xynz and 66% identity to *Cellulomonas fimi* xylanase B. This peptide shoved 60% identity with the thermostable 50 kDa xylanase sequence of *Actinomadura flexuosa* (CA 2,154,945). The 13 amino acid peptide 54 kDaB (Table 4) showed 76% identity to the xylanase xynF of *Pseudomonas fluorescens* and 69% identity to the xylanase xynB of *Cellovibrio mixtus* and xylanase xynB from *Thermotoga neapolitana* as well as xylanase xyn33 of *Megnaporthea grisea*. A 70% identity was also found to the sequence of the thermostabile 50 kDa xylanase of *Actinomadura flexuosa* xylanase (CA 2,154, 945).

TABLE 4

```
24kDa    GLY-GLY-THR-PRO-SER-SER-THR-GLY-TRP-HIS-GLY-GLY-TYR-    (SEQ ID NO:1)
          1   2   3   4   5   6   7   8   9  10  11  12  13

PHE-TYR-SER-PHE-TRP-THR-ASP-X-GLY-GLY-GLU-VAL-ASN-
         14  15  16  17  18  19  20 21 22  23  24  25  26

TYR-TRP-ASN-GLY-ASN-ASN-GLY-ASN-TYR-GLY-
         27  28  29  30  31  32  33  34  35  36

54kDaA   GLY-ALA-PRO-ILE-ASP-GLY-VAL-X-PHE-GLN-X-HIS-LEU-ILE-   (SEQ ID NO:2)
          1   2   3   4   5   6   7  8  9  10 11  12  13  14

VAL-
         15

54kDaB   LEU-TYR-TYR-ASN-ASP-TYR-ASN-LEU-GLU-TYR-X-ASN-ALA-    (SEQ ID NO:3)
          1   2   3   4   5   6   7   8   9  10 11  12  13
```

Temperature and pH Profiles of Purified Xylanases

The temperature and pH profiles of the purified xylanases (incubation time 60 min) are shown in FIG. 3 (A to D). Apparently the 22 kDa xylanase (FIG. 3A) is less thermostable than the 30 (FIG. 3B), 33 (FIG. 3C) and 54 kDa (FIG. 3D) xylanases, especially at higher pH values. The 54 kDa xylanase showed an maximum activity during the 1 h incubation at 80° C. and pH 6.2. The respective values for the 33 kDa xylanase was 70° C. and pH 5.2 and for the 30 kDa xylanase 70° C. and pH 5.2–6.2. The 22 kDa xylanase showed maximum activity at 60° C. and pH 6.2.

Example 6
An ECF Bleaching Experiment Using 22 kDa, 33 kDa and 54 kDa Xylanases purified from *Chaetomium thermophilum* ALKO4265

A bleaching experiment was carried out to determine the usefulness of 22 kDa. 33 kDa and 54 kDa xylanases purified from *Chaetomium thermophilum* ALKO4265 (Example 5) in ECF (elementary chlorine free) bleaching of kraft pulp.

Purified 22 kDa, 33 kDa and 54 kDa xylanases (Example 5) were added to Finnish oxygen-delignified softwood kraft pulp (kappa number 15, viscosity 930 ml/g and brightness 33%) in the amount of 150 nkat/g of pulp dry matter. The enzyme treatments were done at pH 7 and 70° C. for one hour. Reference pulp was kept under the same conditions without enzyme addition. After the enzyme treatments bleaching was performed with $D_0ED_1$ sequence, where $D_0$ means the first chlorine dioxide stage, E means alkaline extraction and $D_1$ means the second chlorine dioxide stage. Bleaching conditions and results are shown in Table 5.

TABLE 5

|  | Reference | 22 kDa | 33 kDa | 54 kDa |
| --- | --- | --- | --- | --- |
| Enzyme treatment |  |  |  |  |
| Consistency, % | 3 | 3 | 3 | 3 |
| Retention time, hours | 1 | 1 | 1 | 1 |
| Enzyme dosage, nkat/g | 0 | 150 | 150 | 150 |
| Temperature, ° C. | 70 | 70 | 70 | 70 |
| pH, start/end | 6.9/7.3 | 7.1/7.4 | 7.1/7.4 | 6.9/7.3 |
| $D_0$-stage |  |  |  |  |
| Consistency, % | 3 | 3 | 3 | 3 |
| Retention time, hours | 1 | 1 | 1 | 1 |
| Temperature, ° C. | 60 | 60 | 60 | 60 |
| $ClO_2$-dosage, % | 2.25 | 2.25 | 2.25 | 2.25 |
| $ClO_2$ consumed, % | 2.24 | 2.24 | 2.23 | 2.23 |
| pH, start/end | 3.0/2.5 | 3.0/2.5 | 2.9/2.5 | 2.9/2.5 |
| E-stage |  |  |  |  |
| Consistency, % | 10 | 10 | 10 | 10 |
| Retention time, hours | 1 | 1 | 1 |  |
| Temperature, ° C. | 70 | 70 | 70 | 70 |
| NaOH, % | 1.4 | 1.4 | 1.4 | 1.4 |
| pH at the end | 10.8 | 10.8 | 10.8 | 10.9 |
| Bnghtness, % | 55.8 | 59.6 | 60.1 | 60.2 |
| Kappa number | 6.3 | 5.3 | 5.1 | 5.0 |
| $D_1$-stage |  |  |  |  |
| Consistency, % | 10 | 10 | 10 |  |

TABLE 5-continued

|  | Reference | 22 kDa | 33 kDa | 54 kDa |
| --- | --- | --- | --- | --- |
| Retention time, hours | 3 | 3 | 3 | 3 |
| Temperature, ° C. | 60 | 60 | 60 | 60 |
| $ClO_2$-dosage, % | 2.0 | 2.0 | 2.0 | 2.0 |
| $ClO_2$ consumed, % | 2.0 | 2.0 | 2.0 | 2.0 |
| pH at the end | 2.9 | 2.7 | 2.7 | 2.7 |
| Brightness, % | 78.3 | 81.5 | 82.2 | 82.4 |
| Viscosity, ml/g | 900 | 900 | 840* | 730* |

As can be seen in Table 5, after the pretreatment at pH 7 and 70° C. with *Chaetomium thermophilum* ALKO4265 xylanases 22 kDa, 33 kDa and 54 kDa, lignin removal in pulps was enhanced (as evidenced by the reduction of kappa numbers) when compared with the reference pulp. Also the brightness values of the final pulps were 3–4 units higher than reference, where enzyme was not used, although the consumption of chlorine dioxide stayed on the same level. The reduction in viscosity with 33 kDa (*) and 54 kDa (*) xylanase pretreatment was due to contaminating cellulase activity present in these enzyme preparations.

Example 7

A TCF Bleaching Experiment using xylanases from the fungus *Chaetomium thermophilum*

A bleaching experiment can be carried out to determine the usefulness of *Chaetomium thermophilum* xylanases in TCF (totally chlorine free) bleaching of pulp.

Xylanase preparations are added to softwood or hardwood pulp in the amount of 20–200 nkat/g of pulp dry matter. The enzyme treatments are performed at pH 5–8 and at 50–80° C. for one to three hours. Reference pulp is kept under the same conditions without enzyme addition. After the enzyme treatments bleaching can be performed for example with QP, QPP or QPPP sequence (also other suitable sequences can be used), where Q stands for chelation stage and P stands for hydrogen peroxide stage.

What is claimed is:

1. A method for degrading a xylan-containing substrate, said method comprising contacting said substrate with a cell-free composition comprising one or more of the following Chaetomium thermophilum xylanases:

(i) a *Chaetomium thermophilum* xylanase having a molecular weight on SDS-PAGE of about 54 kDa, a pI of about 8.9, and a maximum activity at about pH 6.2 in the temperature range of 60 to 80° C., and at about 80° C. in the pH range 6.2 to 7.9;

(ii) a *Chaetomium thermophilum* xvlanase having a molecular weight on SDS-PAGE of about 33 kDa, a pI of about 8.3, and a maximum activity at about pH 5.2 in the temperature range of 50 to 80° C., and at about 70° C. in the pH range 5.2 to 7.9;

(iii) a *Chaetomium thermophilum* xvlanase having a molecular weight on SDS-PAGE of about 30 kDa, a pI of about 8.7, and a maximum activity between about pH 5.2–6.2 in the temperature range of 50 to 80° C., and at about 70° C. in the pH range 5.2 to 7.9; or (iv) a *Chaetomium thermophilum* xylanase having a molecular weight on SDS-PAGE of about 22 kDa, a pI of about 9.3, and a maximum activity at about pH 6.2 in the temperature range of 50 to 80° C., and about 60° C. in the pH range 5.2 to 7.9.

2. The method of claim 1, wherein said *Chaetomium thermophilum* xylanase in said cell-free composition is said 54 kDa xylanase.

3. The method of claim 1, wherein said *Chaetomiurn thermophilum* xylanase in said cell-free composition is said 33 kDa xylanase.

4. The method of claim 1, wherein said *Chaelomium thermophilum* xylanase in said cell-free composition is said 30 kDa xylanase.

5. The method of claim 1, wherein said *Chaetomium thermophilum* xylanase in said cell-free composition is said 22 kDa xylanase.

6. A method for degrading a xylan-containing substrate, said method comprising contacting said substrate with one or more of the following isolated *Chaetomium thermophilum* xylanases:
   (i) a *Chaetomium thermophilum* xylanase having a molecular weight on SDS-PAGE of about 54 kDa, a pI of about 8.9, and a maximum activity at about pH 6.2 in the temperature range of 60 to 80° C., and at about 80° C. in the pH range 6.2 to 7.9;
   (ii) a *Chaetomium thermophilum* xylanase having a molecular weight on SDS-PAGE of about 33 kDa, a pI of about 8.3, and a maximum activity at about pH 5.2 in the temperature range of 50 to 80° C., and at about 70° C. in the pH range 5.2 to 7.9;
   (iii) a *Chaetomium thermophilum* xylanase having a molecular weight on SDS-PAGE of about 30 kDa, a pI of about 8.7, and a maximum activity between about pH 5.2–6.2 in the temperature range of 50 to 80° C., and at about 70° C. in the pH range 5.2 to 7.9; or
   (iv) a *Chaetomium thermophilum* xylanase having a molecular weight on SDS-PAGE of about 22 kDa, a pI of about 9.3, and a maximum activity at about pH 6.2 in the temperature range of 50 to 80° C., and at about 60° C. in the pH range 5.2 to 7.9.

7. The method of claim 6, wherein said isolated *Chaetomium thermophilum* xylanase is said 54 kDa xylanase.

8. The method of claim 6, wherein said isolated *Chaetomium thermophilum* xylanase is said 33 kDa xylanase.

9. The method of claim 6, wherein said isolated *Chaetomium thermophilum* xylanase is said 30 kDa xylanase.

10. The method of claim 6, wherein said isolated *Chaetomium thermophilum* xylanase is said 22 kDa xylanase.

11. A method for treating wood-derived pulp or fiber, said method comprising adding a cell-free composition comprising one or more of the following *Chaetomium thermophilum* xylanases:
   (i) a *Chaetomium thermophilum* xylanase having a molecular weight on SDS-PAGE of about 54 kDa, a pI of about 8.9, and a maximum activity at about pH 6.2 in the temperature range of 60 to 80° C., and at about 80° C. in the pH range 6.2 to 7.9;
   (ii) a *Chaetomium thermophilum* xylanase having a molecular weight on SDS-PAGE of about 33 kDa, a pI of about 8.3, and a maximum activity at about pH 5.2 in the temperature range of 50 to 80° C., and at about 70° C. in the pH range 5.2 to 7.9:
   (iii) a *Chaetomium thermophilum* xylanase having a molecular weight on SDS-PAGE of about 30 kDa, a pI of about 8.7, and a maximum activity between about pH 5.2–6.2 in the temperature range of 50 to 80° C., and at about 70° C. in the pH range 5.2 to 7.9; or
   (iv) a *Chaetomium thermophilum* xylanase having a molecular weight on SDS-PAGE of about 22 kDa, a pI of about 9.3, and a maximum activity at about pH 6.2 in the temperature range of 50 to 80° C., and at about 60° C. in the pH range 5.2 to 7.9
to a wood-derived mechanical or chemical pulp or secondary fiber.

12. The method of claim 11, wherein said *Chaetomium thermophilum* xylanase in said cell-free composition is said 54 kDa xylanase.

13. The method of claim 11, wherein said *Chaetomium thermophilum* xylanase in said cell-free composition is said 33 kDa xylanase.

14. The method of claim 11, wherein said *Chaetomium thermophilum* xylanase in said cell-free composition is said 30 kDa xylanase.

15. The method of claim 11, wherein said *Chaetomium thermophilum* xylanase in said cell-free composition is said 22 kDa xylanase.

16. A method for treating wood-derived pulp or fiber, said method comprising adding one or more of the following isolated *Chaetomium thermophilum* xylanases;
   (i) a *Chaetomium thermophilum* xylanase having a molecular weight on SDS-PAGE of about 54 kDa, a pI of about 8.9, and a maximum activity at about pH 6.2 in the temperature range of 60 to 80° C., and at about 80° C. in the pH range 6.2 to 7.9;
   (ii) a *Chaetomium thermophilum* xylanase having a molecular weight on SDS-PAGE of about 33 kDa, a pI of about 8.3, and a maximum activity at about pH 5.2 in the temperature range of 50 to 80° C., and at about 70° C. in the pH range 5.2 to 7.9;
   (iii) a *Chaetomium thermophilum* xylanase having a molecular weight on SDS-PAGE of about 30 kDa, a pI of about 8.7, and a maximum activity between about pH 5.2–6.2 in the temperature range of 50 to 80° C., and at about 70° C. in the pH range 5.2 to 7.9; or
   (iv) a *Chaetomium thermophilum* xylanase having a molecular weight on SDS-PAGE of about 22 kDa, a pI of about 9.3, and a maximum activity at about pH 6.2 in the temperature range of 50 to 80° C., and at about 60° C. in the pH range 5.2 to 7.9
to a wood-derived mechanical or chemical pulp or secondary fiber.

17. The method of claim 16, wherein said isolated *Chaetomium thermophilum* xylanase is said 54 kDa xylanase.

18. The method of claim 16, wherein said isolated *Chaetomium thermophilum* xylanase is said 33 kDa xylanase.

19. The method of claim 16, wherein said isolated *Chaetomium thermophilum* xylanase is said 30 kDa xylanase.

20. The method of claim 16, wherein said isolated *Chaetomium thermophilum* xylanase is said 22 kDa xylanase.

21. A method for bleaching pulp, said method comprising contacting said pulp with a cell-free composition comprising one or more of the following *Chaetomium thermophilum* xylanases:
   (i) a *Chaetomium thermophilum* xylanase having a molecular weight on SDS-PAGE of about 54 kDa, a pI of about 8.9, and a maximum activity at about pH 6.2 in the temperature range of 60 to 80° C., and at about 80° C. in the pH range 6.2 to 7.9;
   (ii) a *Chaetomium thermophilum* xylanase having a molecular weight on SDS-PAGE of about 33 kDa, a pI of about 8.3, and a maximum activity at about pH 5.2 in the temperature range of 50 to 80° C., and at about 70° C. in the pH range 5.2 to 7.9;
   (iii) a *Chaetomium thermophilum* xylanase having a molecular weight on SDS-PAGE of about 30 kDa, a pI of about 8.7, and a maximum activity between about pH 5.2–6.2 in the temperature range of 50 to 80° C., and at about 70° C. in the pH range 5.2 to 7.9; or
   (iv) a *Chaetomium thermophilum* xylanase having a molecular weight on SDS-PAGE of about 22 kDa, pI of about 9.3, and a maximum activity at about pH 6.2 in the temperature range of 50 to 80° C., and at about 60° C. in the pH range 5.2 to 7.9.

22. The method of claim 21, wherein said *Chaetomium thermophilum* xylanase in said cell-free composition is said 54 kDa xylanase.

23. The method of claim 21, wherein said *Chaetomium thermophilum* xylanase in said cell-free composition is said 33 kDa xylanase.

24. The method of claim 21, wherein said *Chaetomium thermophilum* xylanase in said cell-free composition is said 30 kDa xylanase.

25. The method of claim 21, wherein said *Chaetomium thermophilum* xylanase in said cell-free composition is said 22 kDa xylanase.

26. A method for bleaching pulp, said method comprising contacting said pulp with one or more of the following isolated *Chaetomium thermophilum* xylanases;

(i) a *Chaetomium thermoyhilum* xylanase having a molecular weight on SDS-PAGE of about 54 kDa, a pI of about 8.9, and a maximum activity at about pH 6.2 in the temperature range of 60 to 80° C., and at about 80° C. in the pH range 6.2 to 7.9;

(ii) a *Chaetomium thermoyhilum* xylanase having a molecular weight on SDS-PAGE of about 33 kDa, a pI of about 8.3, and a maximum activity at about pH 5.2 in the temperature range of 50 to 80° C., and at about 70° C. in the pH range 5.2 to 7.9;

(iii) a *Chaetomium thermophilum* xylanase having a molecular weight on SDS-PAGE of about 30 kDa, a pI of about 8.7, and a maximum activity between about pH 5.2–6.2 in the temperature range of 50 to 80° C., and at about 70° C. in the pH range 5.2 to 7.9; or (iv) a *Chaetomium thermophilum* xylanase having a molecular weight on SDS-PAGE of about 22 kDa, a pI of about 9.3, and a maximum activity at about pH 6.2 in the temperature range of 50 to 80° C., and at about 60° C. in the pH range 5.2 to 7.9.

27. The method of claim 26, wherein said isolated *Chaetomium thermophilum* xylanase is said 54 kDa xylanase.

28. The method of claim 26, wherein said isolated *Chaetomium thermophilum* xylanase is said 33 kDa xylanase.

29. The method of claim 26, wherein said isolated *Chaetomium thermophilum* xylanase is said 30 kDa xylanase.

30. The method of claim 26, wherein said isolated *Chaetomium thermophilum* xylanase is said 22 kDa xylanase.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 36 amino acids
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: Chaetomium thermophilum
      (B) STRAIN: CBS730.95

(ix) FEATURE:
      (A) NAME/KEY: Peptide
      (B) LOCATION:1..36
      (D) OTHER INFORMATION:/label= 24kDa_peptide_A (xi) SEQUENCE DESCRIPTION: SEQ ID NO: 1:

```
    Gly Gly Thr Pro Ser Ser Thr Gly Trp His Gly Gly Tyr Phe Tyr Ser
    1               5                   10                  15

Phe Trp Thr Asp Xaa Gly Gly Glu Val Asn Tyr Trp Asn Gly Asn Asn
                    20                  25                  30

Gly Asn Tyr Gly
                35
```

(2) INFORMATION FOR SEQ ID NO: 2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Chaetomium thermophilum
        (B) STRAIN: CBS730.95

(ix) FEATURE:
        (A) NAME/KEY: Peptide
        (B) LOCATION:1..15
        (D) OTHER INFORMATION:/label= 54kDa_peptide_A (xi) SEQUENCE DESCRIPTION: SEQ ID NO: 2:

```
    Gly Ala Pro Ile Asp Gly Val Xaa Phe Gln Xaa His Leu Ile Val
    1               5                   10                  15
```

(2) INFORMATION FOR SEQ ID NO: 3:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Chaetomium thermophilum
        (B) STRAIN: CBS730.95

(ix) FEATURE:
        (A) NAME/KEY: Peptide
        (B) LOCATION:1..13
        (D) OTHER INFORMATION:/label= 54kDa_peptide_B (xi) SEQUENCE DESCRIPTION: SEQ ID NO: 3:

```
    Leu Tyr Tyr Asn Asp Tyr Asn Leu Glu Tyr Xaa Asn Ala
    1               5                   10
```